United States Patent [19]

Saitoh et al.

[11] Patent Number: 5,063,048
[45] Date of Patent: Nov. 5, 1991

[54] UV LIGHT-ABSORBING SKIN-PROTECTING COMPOSITION

[75] Inventors: Izumi Saitoh, Nishinomiya; Yoshio Sasaki, Takefu, both of Japan

[73] Assignees: Shionogi & Co., Ltd., Osaka; Nisshin Chemical Industry Co., Ltd., Fukui, both of Japan

[21] Appl. No.: 550,540

[22] Filed: Jul. 10, 1990

[30] Foreign Application Priority Data

Jul. 10, 1989 [JP] Japan .................. 1-177714

[51] Int. Cl.$^5$ .................. A61K 7/42; C08F 226/06
[52] U.S. Cl. .................. 424/59; 526/261
[58] Field of Search .................. 526/261; 424/59

[56] References Cited

U.S. PATENT DOCUMENTS

| | | | |
|---|---|---|---|
| 4,166,109 | 8/1979 | Jacquet et al. | 424/59 |
| 4,233,430 | 11/1980 | Jacquet et al. | 526/259 |
| 4,938,964 | 7/1990 | Sakai et al. | 424/443 |

Primary Examiner—Joseph L. Schofer
Assistant Examiner—Wu C. Cheng
Attorney, Agent, or Firm—Wenderoth, Lind & Ponack

[57] ABSTRACT

A UV light-absorbing skin-protecting composition which comprises an acrylic copolymer comprising (A) a compound of the formula:

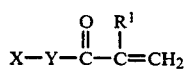

wherein $R^1$ is a hydrogen atom or a methyl group, X is a group of the formula:

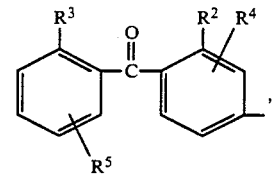

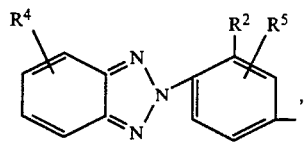

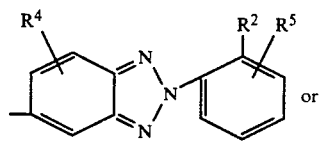

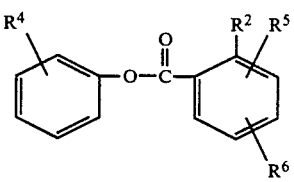

in which
$R^2$ is a hydroxy group, $R^3$ is a hydrogen atom or hydroxy group, $R^4$ and $R^5$ are the same or different and each is a hydrogen atom, a lower alkyl group, a lower alkoxy group, a halogen atom, a nitro group, a carboxyl group, a sulfonic acid group or a sulfonamide group and $R^6$ is a single bond or a methylene group, Y is —O—, —NH— or a group of the formula:

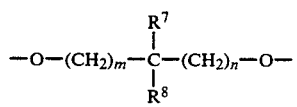

in which $R^7$ is a hydrogen atom or a lower alkyl group, $R^8$ is a hydrogen atom or a hydroxy group, and m and n are the same or different and is each 0 or 1, (B), 40 to 75% by weight of an alkyl acrylate, (C) 10 to 40% by weight of an alkyl methacrylate, and (D) 5 to 30% by weight of a monoethylenically unsaturated monomer having a carboxyl group; and a medium.

10 Claims, 1 Drawing Sheet

---+--- EXAMPLE 1
---×--- EXAMPLE 2
---*--- EXAMPLE 3
---+--- EXAMPLE 4
---○--- COMP. EX. 1

UV LIGHT-ABSORBING SKIN-PROTECTING COMPOSITION

BACKGROUND OF THE INVENTION

1. Field of the Invention

The present invention relates to a UV light-absorbing skin-protecting composition comprising an acrylic copolymer and a medium.

2. Description of the Related Art

There are known skin-protecting agents which protect human skin from damage. The protecting agent is applied to the skin by coating or spraying to form a film which protects the skin. The skin-protecting agent is required to protect the skin from chemicals or other irritative materials, and light, in particular, UV light.

U.S. Pat. No. 4,874,830 and Japanese Patent Kokai Publication Nos. 104909/1988 and 108013/1988 disclose skin-protecting agents for protecting the skin of persons who wash dishes or apparatus with neutral detergents at home or in restaurants, hospitals, beauty shops and the like, which agents comprise an ethyl acrylate-methacrylic acid copolymer. The proposed skin-protecting agents can effectively block many irritative materials, but are not intended to shield UV light. Japanese Patent Publication Nos. 93220/1987 and 198612/1987 propose skin-protecting agents which shield UV light. The proposed skin-protecting agents have good UV light-shielding effect but inferior effect for blocking the irritative materials.

Japanese Patent Publication No. 27737/1968 and Japanese Patent Kokai Publication No. 139958/1988 disclose paints comprising a benzophenone compound. The composition of the paint is intended to improve stability of the paint itself and cannot be used as a skin-protecting agent.

SUMMARY OF THE INVENTION

An object of the present invention is to provide a skin-protecting composition which forms a film effectively blocking irritative materials and shielding UV light.

This and other objects are achieved by a UV light-absorbing skin-protecting composition which comprises:

an acrylic copolymer comprising (A) 1 to 15% by weight of a compound of the formula:

wherein $R^1$ is a hydrogen atom or a methyl group, X is a group of the formula:

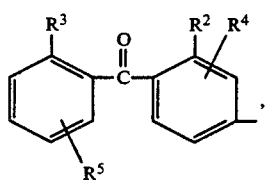

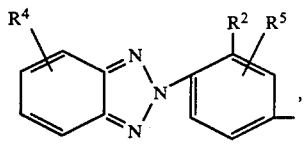

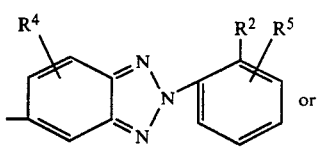

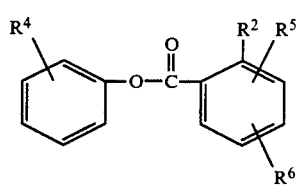

in which $R^2$ is a hydroxy group, $R^3$ is a hydrogen atom or hydroxy group, $R^4$ and $R^5$ are the same or different and each is a hydrogen atom, a lower alkyl group, a lower alkoxy group, a halogen atom, a nitro group, a carboxyl group, a sulfonic acid group or a sulfonamide group, and $R^6$ is a single bond or a methylene group, Y is —O—, —NH— or a group of the formula:

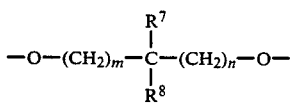

in which $R^7$ is a hydrogen atom or a lower alkyl group, $R^8$ is a hydrogen atom or a hydroxy group, and m and n are the same or different and each is 0 or 1, (B) 40 to 75% by weight of an alkyl acrylate, (C) 10 to 40% by weight of an alkyl methacrylate, and (D) 5 to 30% by weight of a monoethylenically unsaturated monomer having a carboxyl group; and a medium.

DETAILED DESCRIPTION OF THE INVENTION

Figure 1:
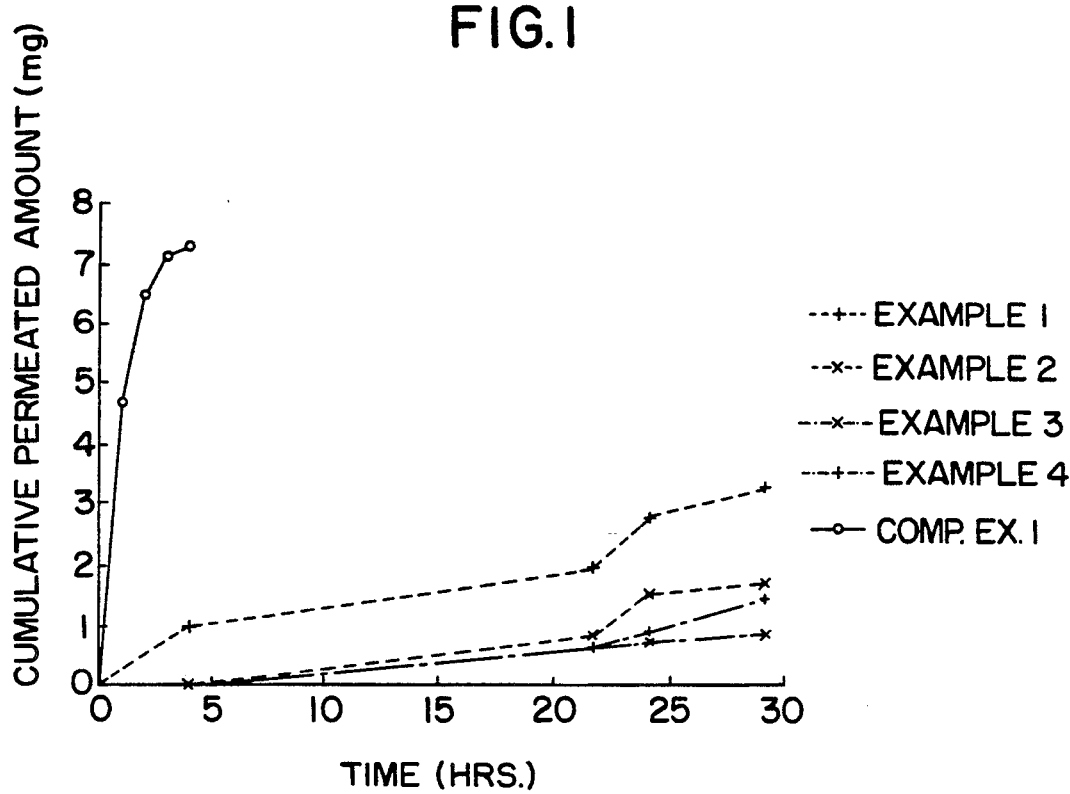
FIG. 1 is a graph showing the cumulative permeated amounts of benzyl alcohol through films.

Typical structures of the compounds (A) having the benzophenone group are as follows:

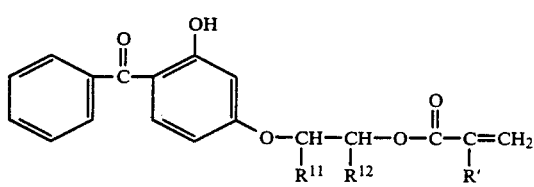

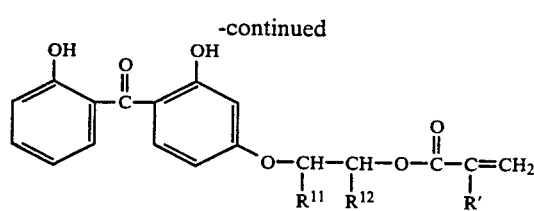

in which R¹¹ and R¹² are independently a hydrogen atom or a methyl group provided that at least one of them is a hydrogen atom, and R' is a hydrogen atom or a methyl group.

Typical structures of the compounds (A) having the benzotriazole group are as follows:

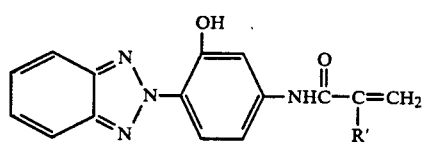

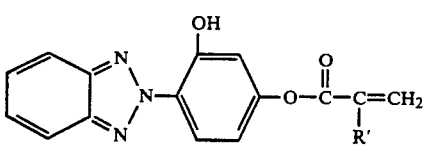

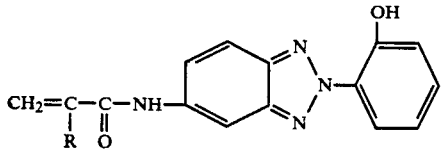

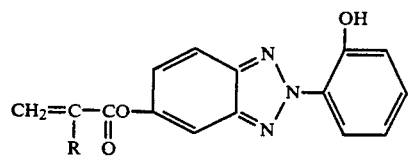

Typical structures of the compounds (A) having the salicylate group are as follows:

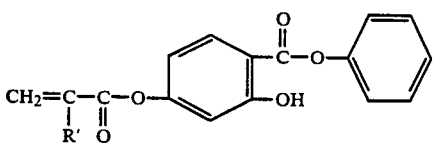

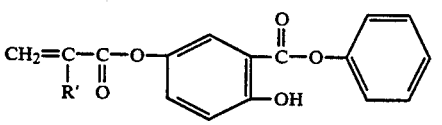

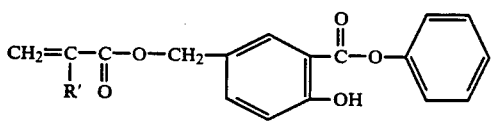

The benzene ring of the above compounds may have other substituents. Specific examples of the other substituent are lower alkyl, lower alkoxy, halogen, carboxy, sulfonic acid, sulfonamide and the like.

Herein, the "lower" alkyl or alkoxy group means an alkyl or alkoxy group having 1 to 3 carbon atoms.

Specific examples of the component (A) are:

Benzophenone type compounds 2-hydroxy-4-(2-methacryloyloxyethoxy)benzophenone,
2-hydroxy-4-(2-acryloyloxyethoxy)benzophenone,
2-hydroxy-4-(2-methacryloyloxybutoxy)benzophenone,
2-hydroxy-4-(2-acryloyloxybutoxy)benzophenone,
2-hydroxy-4-(3-methacryloyloxy-2-hydroxypropoxy)benzophenone,
2-hydroxy-4-(3-acryloyloxy-2-hydroxypropoxy)benzophenone,
2-hydroxy-4-(2-methacryloyloxy-2-methylethoxy)benzophenone,
2-hydroxy-4-(2-acryloyloxy-2-methylethoxy)benzophenone,
2-hydroxy-4-(2-methacryloyloxy-1-methylethoxy)benzophenone,
2-hydroxy-4-(2-acryloyloxy-1-methylethoxy)benzophenone,
2,2'-dihydroxy-4'-methoxy-4-(2-methacryloyloxyethoxy)benzophenone,
2,2'-dihydroxy-4'-methoxy-4-(2-acryloyloxyethoxy)benzophenone, Benzotriazole type compounds 2-(4-methacryloxy-2-hydroxyphenyl)benzotriazole,
2-(4-methacrylamide-2-hydroxyphenyl)benzotriazole,
2-(2'-hydroxy-phenyl)-5-methacryloxybenzotriazole, Salicylate type compounds phenyl 2-hydroxy-4-acryloxybenzoate,
phenyl 2-hydroxy-4-methacryloxybenzoate,
phenyl 2-hydroxy-5-acryloxybenzoate, and
phenyl 2-hydroxy-5-methacryloxybenzoate.

The amount of the component (A) is 1 to 15% by weight based on the total weight of components (A) to (D). When this amount is smaller than 1% by weight, the UV light-shielding property is insufficient. When this amount is larger than 15% by weight, the copolymer is not homogenous.

The UV light-absorbing acrylic or methacrylic acid derivative may be prepared by a conventional method. For example, the benzophenone type compound is prepared by esterifying the hydroxyalkoxy group at the 4-position with acrylic acid or methacrylic acid according to the known method which is disclosed in, for example, U.S. Pat. No. 3,313,866, the disclosure of which is hereby incorporated by reference.

The benzotriazole or salicylate type acrylic or methacrylic derivative may be prepared by a similar method to the above. The benzotriazole type compound may be prepared by introduction of the acryloyloxy, methacryloyloxy, acrylamide or methacrylamide group in the known manner which is disclosed in, for example, U.S. Pat. No. 3,159,646, the disclosure of which is hereby incorporated by reference.

The salicylate type compound may be prepared by reacting acrylic or methacrylic chloride with salicylic acid or its derivative, or substituting a chloromethylated compound with sodium acrylate or methacrylate, as disclosed in, for example, U.S. Pat. No. 3,141,903.

The alkyl acrylate (B) is preferably an alkyl acrylate having 1 to 6 carbon atoms in the alkyl group, more particularly methyl acrylate, ethyl acrylate, propyl acrylate and butyl acrylate.

The alkyl methacrylate (C) is preferably an alkyl methacrylate having 1 to 6 carbon atoms in the alkyl group, more preferably, methyl methacrylate, ethyl methacrylate and propyl methacrylate.

The alkyl acrylate (B) and the alkyl methacrylate (C) provide the acrylic copolymer with solubility in solvents, a film-forming property, and compatibility and adhesivity to the skin or other materials. Since the alkyl acrylate is soft and the alkyl methacrylate is rigid, flexibility of the film of acrylic copolymer of the present invention can be adjusted in a wide range by changing the ratio of these two components in the copolymer.

The amount of the alkyl acrylate (B) is 40 to 75% by weight, preferably 50 to 70% by weight based on the total weight of the components (A) to (D). When this amount is less than 40% by weight, the film has poor flexibility. When this amount is larger than 75% by weight, the film becomes tacky and has insufficient strength.

The amount of the alkyl methacrylate (C) is 10 to 40% by weight, preferably 15 to 30% by weight based on the total weight of the components (A) to (D). When this amount is outside the above range, the film has poor flexibility.

Examples of the monoethylenically unsaturated monomer having a carboxyl group (D) are acrylic acid, methacrylic acid, crotonic acid, itaconic acid, maleic acid, fumaric acid, and half esters of maleic acid and fumaric acid. Among them, methacrylic acid is preferred.

The monomer (D) provides the copolymer with adhesivity to the skin and swellability or dispersibility in weak alkali such as an aqueous solution of soap, an amine or aqueous ammonia, whereby the removal of the copolymer film from the skin is made easier.

The amount of the monomer (D) is 5 to 30% by weight, preferably 10 to 20% by weight based on the total weight of the components (A) to (D). When this amount is less than 5% by weight, the removal of the film is not easy. When this amount is larger than 30% weight, the film of the copolymer lacks water resistance and flexibility.

The acrylic copolymer of the present invention may comprise other comonomers in addition to the above essential components. Examples of the other comonomer are vinyl monomers such as vinyl acetate, 2-hydroxyethyl methacrylate, N-vinyl pyrrolidone, etc. The amount of the other comonomer is not larger than 20 parts by weight per 100 parts by weight of the total weight of the components (A) to (D).

The acrylic copolymer of the present invention has an average molecular weight of, in general, 50,000 to 1,300,000, preferably 100,000 to 800,000 measured by GPC.

When the average molecular weight is less than 50,000, the copolymer film has insufficient tensile strength and unsatisfactory functionality, while when it is larger than 1,300,000, the skin-protecting composition has increased viscosity so that spinnability occurs during application of the composition to the skin.

The acrylic copolymer of the present invention may be prepared by copolymerizing the above monomers by a per se conventional method. The polymerization method may be solution polymerization or emulsion polymerization.

For example, the solution polymerization is carried out by heating the monomer mixture in a solvent in the presence of a polymerization initiator while stirring.

Examples of the solvent are methanol, ethanol, isopropanol, acetone, methyl ethyl ketone, methyl acetate, ethyl acetate, ethyleneglycol monoalkyl ether and the like. Examples of the polymerization initiator are solvent-soluble ones such as dibenzoyl peroxide, cumene hydroperoxide, diisopropyl peroxydicarbonate and azobisisobutyronitrile.

The emulsion polymerization is carried out by heating a dispersion of an emulsifier, a water-soluble polymerization initiator and the monomer mixture in water while stirring. Preferred examples Of the emulsifier are anionic or nonionic surfactants such as sodium laurylsulfate, sodium N-lauroylsarcosinate, polyoxyethylene lauryl ether, polyoxyethylenesorbitan monooleate, sorbitan sesquioleate, glyceryl monostearate, aliphatic acid esters with sucrose and the like. Examples of the water-soluble polymerization initiator are ammonium persulfate, potassium persulfate, hydrogen peroxide, tert.-butyl hydroperoxide and the like. Optionally, a reducing agent such as sodium hydrogensulfite and L-ascorbic acid can be additionally used.

The solution or emulsion of the copolymer obtained from the polymerization process may be used as the skin-protecting composition of the present invention. Preferably, to the solution of the copolymer, water, ethylene glycol or a hydrocarbon base non-solvent (e.g. n-hexane) is added to precipitate the copolymer from the solution. Then, the precipitated copolymer is washed with water or the non-solvent hydrocarbon, purified and cried. The emulsion of the copolymer is coagulated with the addition of an acid or an aqueous solution of a salt such as sodium sulfate and calcium chloride and the coagulated copolymer is washed with water, purified and dried. Then, to the dried copolymer, a suitable medium is added to prepare the skin-protecting composition of the present invention.

The skin-protecting composition of the present invention comprises the acrylic copolymer and a medium and can be in the form of a solution, a cream or a spraying liquid. The medium is preferably a solvent such as a lower alcohol or a solvent which is generally used in the preparation of a lotion, a cream or a spraying liquid. Preferred examples of the medium are ethanol. isopropanol and a mixture of water and ethanol or isopropanol.

Preferably, the skin-protecting composition of the present invention is in the solution form. The concentration of the copolymer in a solution is from 1 to 30% by weight, preferably 5 to 10% by weight. When the mixed solvent of water and an alcohol is used, the ratio of water to the alcohol can vary in a wide range.

The acrylic copolymer of the present invention effectively shields UV light, and prevents permeation of irritative materials such as perillaldehyde, benzyl alcohol, sodium benzoate, benzalkonium chloride, chlorhexidine gluconate, and the like.

When a small amount of the skin-protecting composition is applied to the skin, a very thin film of the copolymer is formed on the skin. The formed film has sufficient water resistance and acid resistance, has good elongation and flexibility, and adheres well to the skin without malaise. In addition, the copolymer is very safe to the skin since it has no or little irritation to the skin.

The formed film can be easily and safely removed from the skin with a weakly alkaline aqueous solution such as an aqueous solution of soap or an alcohol such as ethanol.

PREFERRED EMBODIMENTS OF THE INVENTION

The present invention will be illustrated by following Examples, in which "parts" are by weight unless otherwise indicated.

EXAMPLE 1

In a closed reactor equipped with a stirrer, the internal space of which had been replaced with nitrogen, ethyl acetate (75 parts) was charged, and the internal temperature of the reactor was adjusted at 50° C. To the content of the reactor, diisopropyl peroxydicarbonate (2.0 parts) was added. Then, a mixture of the following monomers and a 0.5% solution of diisopropyl peroxydicarbonate in ethyl acetate (100 parts) were added over 4 hours while keeping the internal temperature of the reactor at 55° C.:

| 1) Benzophenone compound (1) | 2.0 parts |
|---|---|

$$\text{Ph-CO-C}_6\text{H}_3(\text{OH})\text{-OCH}_2\text{-CH}_2\text{-OC(O)-C(CH}_3\text{)=CH}_2$$

| 2) Methyl methacrylate (MMA) | 19.6 parts |
|---|---|
| 3) Methacrylic acid (MAA) | 14.7 parts |
| 4) Ethyl acrylate (EA) | 63.7 parts |

The content of the reactor was stirred a 50° C. for 2 hours and at 77° C. for 3 hours to complete polymerization, followed by cooling to room temperature to obtain a copolymer.

The reaction mixture was poured into a mixer. To the mixture, n-hexane (1000 parts) was gradually added while stirring under shear to precipitate the copolymer, which was recovered by filtration, washed with n-hexane and dried. Yield of the copolymer was 96%. The copolymer had the weight average molecular weight of $11.8 \times 10^4$ (by GPC).

The copolymer was dissolved in ethanol at a concentration of 30% to obtain a transparent solution. The copolymer was also dissolved in a mixture of 70 parts of ethanol and 30 parts of water at a concentration of 30% to obtain a solution.

EXAMPLES 2–5 AND COMPARATIVE EXAMPLES 1–2

In the same manner as in Example 1 but using a monomer mixture shown in Table 1, a copolymer was prepared, and a 30% solution of the copolymer in ethanol was obtained. The monomeric composition (% by weight) and the properties of the copolymer are shown in Table 1.

In Example 5, the following benzophenone type compound (2) was used as the benzophenone type compound.

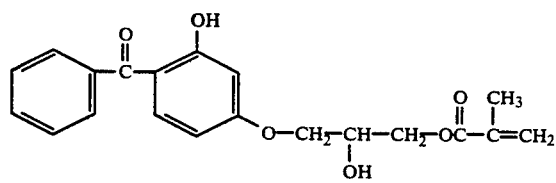

In Comparative Example 1, Hand-Guard (trade mark, a skin-protecting agent manufactured by Shionogi & Co., Ltd.) was used.

EXAMPLE 6

In a closed reactor equipped with a stirrer, deionized water (67.0 parts), isopropanol (1.5 parts) and ferrous sulfate (0.0025 part) were charged, the internal atmosphere was replaced with nitrogen gas and the internal temperature was adjusted at 60° C.

A monomer mixture of the benzophenone type compound (1) as used in Example 1 (5.0 parts), ethyl acrylate (EA) (61.7 parts), methyl methacrylate (MMA) (19.0 parts) and methacrylic acid (MAA) (14.3 parts) was emulsified by means of a homogenizer in deionized water (100 parts) in he presence of sodium laurylsulfate (0.5 part) and Polysolvate 80 (polyoxyethylenesorbitan monooleate) (1.0 part) to prepare an emulsion.

Then, this emulsion, a 0.75% aqueous solution of ammonium persulfate (33.3 parts) and a 0.6% aqueous solution of sodium hydrogensulfite (33.3 parts) were separately dropwise added to the reactor kept at 60° C. over 4 hours. The reaction mixture was further stirred for 2 hours at 60° C. to complete the polymerization to obtain an emulsion of the copolymer.

To the resulting emulsion, dilute sulfuric acid was added to coagulate the copolymer, which was recovered by filtration, washed with water and dried. The copolymer had the weight average molecular weight of $47.2 \times 10^4$.

The copolymer was dissolved in ethanol at a concentration of 15% t obtain a transparent solution.

EXAMPLE 7

In a closed reactor equipped with a stirrer, the internal space of which had been replaced with nitrogen gas, ethyl acetate (75 parts) was charged, and the internal temperature was adjusted at 50° C. To the content of the reactor, diisopropyl peroxydicarbonate (2.0 parts) was added. Then, a mixture of the following monomers and a 0.5 % solution of diisopropyl peroxydicarbonate in ethyl acetate (100 parts) were added over 4 hours while keeping the internal temperature of the reactor at 50° C.:

| 1) Benzophenone type compound (1) | 8.0 parts |
|---|---|
| 2) Butyl acrylate (BA) | 48.0 parts |
| 3) Methyl methacrylate (MMA) | 33.0 parts |
| 4) Acrylic acid (AA) | 11.0 parts |

The content of the reactor was stirred at 50° C. for 2 hours and at 77° C. for 3 hours to complete polymerization, followed by cooling to room temperature.

The reaction mixture was poured into a mixer. To the mixture, n-hexane (1000 parts) was gradually added while stirring under shear to precipitate the purified copolymer, which was recovered by filtration, washed with n-hexane and dried. Yield of the copolymer was 96%. The copolymer had the weight average molecular weight of $18.5 \times 10^4$ (by GPC).

The copolymer was dissolved in ethanol at a concentration of 30% to obtain a transparent solution.

TABLE 1

| Example No | 1 | 2 | 3 | 4 | 5 | 6 | 7 | C. 1 | C. 2 |
|---|---|---|---|---|---|---|---|---|---|
| Compound (1) | 2.0 | 5.0 | 10.0 | 14.3 | | 5.0 | 8.0 | | |
| Compound (2) | | | | | 5.0 | | | | |
| EA | 63.7 | 61.7 | 58.5 | 52.4 | 61.7 | 61.7 | | 85.0 | 65.0 |
| BA | | | | | | | 48.0 | | |
| MMA | 19.6 | 19.0 | 18.0 | 19.0 | 19.0 | 19.0 | 33.0 | | 20.0 |
| MAA | 14.7 | 14.3 | 13.5 | 14.3 | 14.3 | 14.3 | | 15.0 | 15.0 |
| AA | | | | | | | 11.0 | | |
| Av. MW ($\times 10^4$) | 11.6 | 17.2 | 21.5 | 38.9 | 19.1 | 47.4 | 18.5 | 80.0 | 8.5 |

EXPERIMENTS

With each of the solutions of Example 1–6 and Comparative Examples 1 and 2, the following tests were carried out:

1. Film permeability of chemicals

With a table coater (HIRANO KINZOKU CO., LTD.), a film of about 50 μm in thickness was formed from the solution. With the formed film, effect for preventing permeation of chemicals was evaluated in vitro.

In a Franz type cell having a permeation area of 10 cm², the film was attached using a 0.45 μm membrane filter as a support. After filling a receptor cell with purified water, a 1% aqueous solution of the chemical to be tested (1 ml) was charged in a donor cell. Then, an amount of the chemical which permeated to the receptor cell through the film was measured as time passes and a cumulative permeated amount of the chemical was calculated. As a model compound, benzyl alcohol was used.

The cumulative permeated amount of benzyl alcohol is plotted in FIG. 1.

The films formed from the copolymers of Examples 1–4 had much better effect for preventing permeation of the chemical than the film formed from the agent of Comparative Example 1.

2. Transmission of UV light through films

A film was formed from a polymer listed in Table 2 and its UV transmission was evaluated with a double beam self-recording type spectrophotometer UV-300 (manufactured by Shimadzu Corporation). The results are shown in Table 2 and 3.

TABLE 2

| Polymer | Film thickness (μm) | UV light transmission (%) Wavelength (nm) | | | | | | |
|---|---|---|---|---|---|---|---|---|
| | | 400 | 360 | 320 | 300 | 280 | 260 | 240 |
| Example 1 | 50 | 60 | 9 | 0 | 0 | 0 | 1 | 0 |
| UV light-absorbing film *1) | 50 | 86 | 27 | 26 | 25 | 8 | 2 | 0 |
| Polystyrene | 50 | 90 | 89 | 87 | 86 | 78 | 1 | 0 |
| Polyvinyl chloride | 50 | 90 | 87 | 80 | 72 | 1 | 0 | 0 |
| Polyethylene | 50 | 90 | 89 | 87 | 86 | 84 | 84 | 83 |
| Polypropylene | 50 | 91 | 90 | 88 | 87 | 82 | 79 | 76 |
| Com. Ex. 1 + PARSOL *2) | 50 | 91 | 77 | 0 | 0 | 0 | 0 | 0 |

Note:
*1) SC film manufactured by Shobun Laminate Co., Ltd.
*2) PARSOL (trade mark), UV light absorbing agent for cosmetics manufactured by GIVAUDAN, which was used in an amount of 2 parts per 100 parts of the copolymer.

TABLE 3

| Polymer | Film thickness (μm) | UV light transmission (%) Wavelength (nm) | | | | | | | |
|---|---|---|---|---|---|---|---|---|---|
| | | 500 | 400 | 360 | 320 | 300 | 280 | 260 | 240 |
| Example 1 | 18 | 91 | 87 | 19 | 0 | 0 | 0 | 1 | 0 |
| Example 2 | 18 | 90 | 88 | 14 | 0 | 0 | 0 | 1 | 0 |
| Example 3 | 20 | 91 | 88 | 2 | 0 | 0 | 0 | 0 | 0 |
| Example 4 | 12 | 89 | 84 | 1 | 0 | 0 | 0 | 0 | 0 |
| Example 5 | 17 | 92 | 88 | 20 | 0 | 0 | 0 | 1 | 0 |
| Example 6 | 17 | 92 | 90 | 44 | 4 | 3 | 1 | 9 | 1 |
| Co. Ex. 1 | 4 | 18 | 16 | 15 | 15 | 14 | 13 | 13 | 10 |
| Co. Ex. 2 | 16 | 91 | 91 | 90 | 90 | 89 | 88 | 96 | 43 |

From the above results, the films formed from the compositions of the present invention had better UV light-shielding effect than the conventional polymer films.

3. Photolysis of betamethasone valerate

Figure 2:
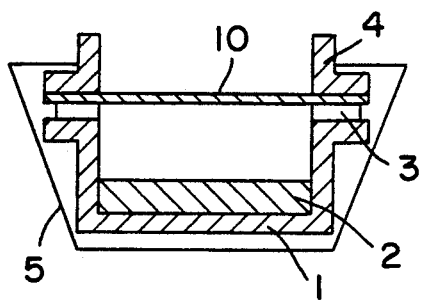
FIG. 2 is a sectional view of an instrument which determines the photolytic property of betamethasone valerate.

By using an apparatus shown in FIG. 2, photolytic property of betamethasone valerate was measured.

In a glass cell 1, Rinderon VG cream 2 (trade mark, manufactured by Shionogi & Co., Ltd. and containing betamethasone valerate) (about 1 g) was weighed. A film 10 to be tested was placed over the glass cell 1 and fixed with a silicone packing 3 and a film presser 4. The periphery of the glass cell was covered with an aluminum foil 5 to shield light. The cell was illuminated with a mercury lamp at 20,000 Lux for 48 hours. During this period, the content of betamethasone valerate (BV) in the cream was measured at intervals. The results are shown in Table 4.

TABLE 4

| Film (Polymer) | Film thickness (μm) | BV content (%) after (hrs) | | | | | |
|---|---|---|---|---|---|---|---|
| | | 0 | 4 | 8 | 16 | 24 | 36 | 48 |
| Example 1 | 50 | 101 | 96 | 85 | 69 | 49 | — | 28 |
| Example 2 | 50 | 101 | — | 99 | 91 | 81 | — | 67 |
| Co. Ex. 2 | 50 | 101 | 73 | 49 | 27 | 11 | 4 | — |
| Co. Ex. 1 | 50 | 101 | 68 | 37 | 18 | 7 | 3 | — |
| SC film | 50 | 101 | — | 78 | 53 | 41 | — | 19 |

Note:
SC film (trade mark): UV light shielding film manufactured by Shobun Laminate Co., Ltd.

The films formed from the copolymers of Examples 1 and 2 had better UV light shielding effect than the conventional films.

What is claimed is:

1. A UV light-absorbing skin-protecting composition which comprises:

an acrylic copolymer comprising (A) 1 to 15% by weight of a compound of the formula:

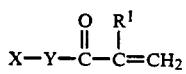

wherein $R^1$ is a hydrogen atom or a methyl group, X is a group of the formula:

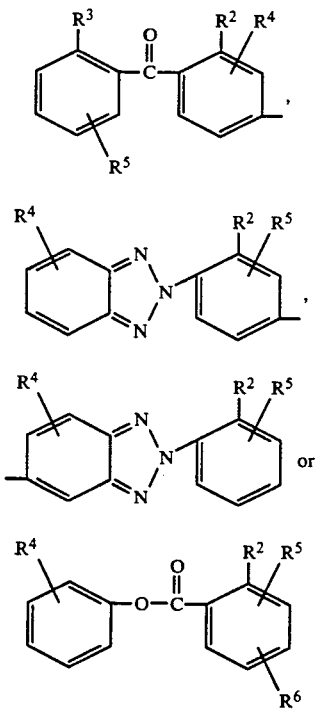

in which $R^2$ is a hydroxy group, $R^3$ is a hydrogen atom or hydroxy group, $R^4$ and $R^5$ are the same or different and each is a hydrogen atom, a lower alkyl group, a lower alkoxy group, a halogen atom, a nitro group, a carboxyl group, a sulfonic acid group or a sulfonamide group, and $R^6$ is a single bond or a methylene group, Y is —O—, —NH— or a group of the formula:

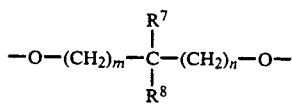

in which $R^7$ is a hydrogen atom or a lower alkyl group, $R^8$ is a hydrogen atom or a hydroxy group, and m and n are the same or different and each is 0 and 1, (B) 40 to 75% by weight of an alkyl acrylate,
(C) 10 and 40% by weight of an alkyl methacrylate, and
(D) 5 to 30% by weight of a monoethylenically unsaturated monomer having a carboxyl group;
and a medium.

2. The UV light-absorbing skin-protecting composition according to claim 1, wherein the amount of the alkyl acrylate (B) is from 50 to 70% by weight based on the total weight of the components (A) to (D).

3. The UV light-absorbing skin-protecting composition according to claim 1, wherein the amount of the alkyl methacrylate (C) is from 15 to 30% by weight based on the total weight of the components (A) to (D).

4. The UV light-absorbing skin-protecting composition according to claim 1, wherein the amount of the monoethylenically unsaturated monomer (D) is from 10 to 20% by weight based on the total weight of the components (A) to (D).

5. The UV light-absorbing skin-protecting composition according to claim 1, wherein the acrylic copolymer has a weight average molecular weight of 50,000 to 1,300,000.

6. The UV light-absorbing skin-protecting composition according to claim 1, which is in a solution form in the medium.

7. The UV light-absorbing skin-protecting composition according to claim 6, wherein the medium is ethanol.

8. The UV light-absorbing skin-protecting composition according to claim 6, wherein the medium is a mixture of water and ethanol.

9. The UV light-absorbing skin-protecting composition according to claim 6, wherein a concentration of the acrylic copolymer in the medium is 1 to 30% by weight.

10. The UV light-absorbing skin-protecting composition according to claim 9, wherein the concentration of the acrylic copolymer is from 5 to 10% by weight.

* * * * *